(12) United States Patent
Suflita et al.

(10) Patent No.: US 9,139,780 B2
(45) Date of Patent: Sep. 22, 2015

(54) METHODS FOR OBTAINING CLEAN ENERGY FROM COAL

(75) Inventors: Joseph Suflita, Norman, OK (US); Mark Nanny, Norman, OK (US); Margarita Mendivelso Castro, Traverse City, MI (US); Jan Sunner, Norman, OK (US)

(73) Assignee: The Board of Regents of The University of Oklahoma, Norman, OK (US)

( * ) Notice: Subject to any disclaimer, the term of this patent is extended or adjusted under 35 U.S.C. 154(b) by 393 days.

(21) Appl. No.: 13/442,430

(22) Filed: Apr. 9, 2012

(65) Prior Publication Data

US 2012/0255725 A1    Oct. 11, 2012

Related U.S. Application Data

(60) Provisional application No. 61/473,562, filed on Apr. 8, 2011.

(51) Int. Cl.
| | |
|---|---|
| *E21B 43/22* | (2006.01) |
| *C09K 8/582* | (2006.01) |
| *C12P 5/02* | (2006.01) |
| *C12P 1/04* | (2006.01) |
| *C10G 3/00* | (2006.01) |
| *E21B 43/00* | (2006.01) |

(52) U.S. Cl.
CPC . *C10G 3/00* (2013.01); *C09K 8/582* (2013.01); *C12P 5/023* (2013.01); *E21B 43/006* (2013.01); *Y02E 50/343* (2013.01)

(58) Field of Classification Search
CPC ....... Y02E 50/343; C12P 5/023; C09K 8/582; E21B 43/006
See application file for complete search history.

(56) References Cited

U.S. PATENT DOCUMENTS 4,845,034 A * 7/1989 Menger et al. ............... 435/167

OTHER PUBLICATIONS

Faison et al.; Biosolubilization of Coal in Aqueous and Non-Aueous Media; pp. 540-547.
Scott et al.; Microbial solubilization of coal.; Biotechnol Prog. Sep. 1986; 2(3):131-9.
Gieg et al.; Bioenergy Production iva Microbial Conversion of Residual Oil to Natural Gas; Applied Environmental Microbiology, vol. 74, No. 10, May 2008; pp. 3022-3029.
Strapoc et al.; Biogeochemistry of Microbial Coal-Bed Methane; Annu. Rev. Earth Planet. Sci. 2011. 39:617-56.
Bailey; The Reactions of Ozone With Organic Compounds; Gem. Rev., 1958 58 (5), pp. 925-1010.
Strapoc; Methanogenic Microbial Degradation of Organic Matter in Indiana Coal Beds; Search and Discovery Article #80013 (2008); 24 pages.
Bitz et al.; Ozonolysis of "Polymer-Type" Material in Coal, Kerogen, and in the Orguell Meteorite: A Preliminary Report; Chemistry: Bitz and Nagy; vol. 56, 1966; pp. 1383-1390.

* cited by examiner

*Primary Examiner* — Zakiya W Bates
(74) *Attorney, Agent, or Firm* — McAfee & Taft (57) ABSTRACT

The present invention provides methods for stimulating or enhancing the conversion of coal to methane. The methods of the current invention subject coal to an oxidation step, for example ozonolysis, thereby converting at least a portion of the coal to partially-oxidized and water-soluble forms of organic matter. Subsequent contact of the oxidized coal components with a suitable inoculum containing a methanogenic microbial community produces methane.

21 Claims, 10 Drawing Sheets

| Coal Sample | Surface Area (m²/g) | | Porosity (cm³/g) | |
|---|---|---|---|---|
| | Unozonated | Ozonated | Unozonated | Ozonated |
| TX | 1.89 | 2.195 | 6.82E-04 | 7.52E-04 |
| OK 4 | 1.347 | 1.355 | 1.56E-04 | 2.98E-04 |
| OK 1 | BDL | BDL | BDL | BDL |
| OK 2 | BDL | BDL | BDL | BDL |

METHODS FOR OBTAINING CLEAN ENERGY FROM COAL

CROSS REFERENCE TO RELATED APPLICATION

This application incorporates by reference and claims the benefit of U.S. Provisional Application 61/473,562 filed on Apr. 8, 2011.

BACKGROUND

With the majority of the available liquid hydrocarbon reservoirs located in politically unstable regions, the need to increase the amount and diversify of energy sources continues to grow. Coal, an abundant natural resource in North America, is not a viable fuel substitute for liquid hydrocarbons. To take advantage of this abundant natural resource, the solid coal must be converted to a more readily usable liquid or gaseous form.

SUMMARY OF THE INVENTION

In one embodiment, the present invention provides a method for converting coal to methane. The method initially contacts coal with an oxidizing agent thereby oxidizing at least a portion of the organic compounds of the coal and producing oxidation products. Following collection of the oxidation products, the method converts at least a portion of the oxidation products to methane by combining the oxidation products with an inoculum containing methanogenic microbial community and allowing the methanogenic microbial community to digest the oxidation products.

In another embodiment, the present invention provides a method for converting coal to methane. According to this embodiment, the method initially forms a slurry of coal and a liquid. Subsequently, at least a portion of the carbonaceous compounds of the coal is oxidized by passing an oxidizing agent through the slurry thereby producing oxidation products. During the oxidation step, the method monitors the pH of the slurry and stops the flow of oxidizing agent to the slurry when the pH of the slurry stabilizes at a pH of less than 6. Subsequently, the method provides for collection of at least part of the liquid portion of the slurry containing the oxidation products to be converted to methane. Following collection of the oxidation products, at least a portion of the oxidation products are converted to methane by combining the oxidation products with an inoculum containing a methanogenic microbial community and allowing the methanogenic microbial community to digest the oxidation products.

In a further embodiment, the present invention provides for the in situ conversion of organic compounds of a subterranean coal seam to methane. This embodiment comprises the steps of contacting the in situ organic compounds of coal with an oxidizing agent thereby oxidizing at least a portion of the in situ organic compounds and producing oxidation products. Following collection of the oxidation products, the methods converts at least a portion of the oxidation products to methane by combining the oxidation products with an inoculum containing a methanogenic microbial community and allowing the methanogenic microbial community to digest the oxidized hydrocarbons.

In yet another embodiment, the present invention provides a method directed to the conversion of converting in situ organic compounds of a subterranean coal seam to methane. This method comprises the steps of initially drilling at least one well into or adjacent to the subterranean coal seam thereby fluid communication between the seam and the surface. Subsequently, the method injects a fluid and an oxidizing agent into the subterranean coal seam. Contacting of the in situ organic compounds of coal with the oxidizing agent oxidizes at least a portion of the compounds producing oxidation products. During the oxidation process, the method provides for monitoring of the fluid within the subterranean coal seam and subsequently stops the injection of oxidizing agent when the pH of the fluid stabilizes at a pH of less than 6. Oxidation products are then collected by extraction from the subterranean coal seam and at least a portion thereof converted to methane by combining the oxidation products with an inoculum containing methanogenic microbial community and allowing the methanogenic microbial community to digest the oxidized hydrocarbons.

DETAILED DISCLOSURE

The present invention provides methods for converting in situ coal beds and extracted ex situ coal to methane. As known to those skilled in the art, various reforming processes can be used to build the methane compound into longer chain, more complex hydrocarbons. Thus, the present invention provides an immediately usable fuel source in the form of gaseous methane and a raw material for producing more complex hydrocarbons.

As noted above, the methods of the present invention provide for the conversion of an in situ coal seam or bed, i.e. a subterranean or surface deposit of coal, to methane. In one embodiment, the present invention treats the in situ deposit of coal to form precursor compounds suitable for extraction and final conversion to methane. In another embodiment, the present invention carries out the complete method on an in situ, subterranean deposit of coal. Finally, the present invention also provides for converting extracted or mined coal to methane. In each embodiment, the present invention initially oxidizes the carbonaceous compounds present in coal to produce simpler compounds such as but not limited to aldehydes, ketones and carboxylic acids. Typically, an ozonolysis step, using ozone gas, will yield the desired compounds. However, any oxidation process capable of producing compounds suitable for digestion in a methanogenesis process will be appropriate for use in the current invention. Suitable oxidizing agents include, but are not limited to, ozone and hydrogen peroxide. Following oxidation, the present invention subsequently concentrates the oxidation products in an effluent followed by incubation of the effluent with a methanogenic inoculum containing microorganisms capable of converting the oxidation products in the effluent to methane.

In Situ Oxidation with Surface Methanogenesis

When practiced on in situ subterranean coal seam, the initial steps of one embodiment of the current invention prepare the coal seam for oxidation via ozonolysis. These steps include drilling at least one and preferably a series of injection and extraction wells. The wells may penetrate into the coal seam or be sufficiently close to provide fluid communication between the surface and the subterranean coal seam. Following drilling of the wells, the coal seam may be optionally fractured by any conventional technique. Fracturing of the coal seam increases the surface area available for ozonolysis treatment and provides enhanced fluid flow through the coal seam.

If the method includes the step of fracturing, by injection of fluids under pressure sufficient to fracture the coal bed, then the fracturing fluid may optionally include an oxidizing agent suitable to oxidize the organic compounds. For example, during fracturing operations, ozone may be added by any convenient method, including bubbling into the fracturing fluid, prior to injection downhole thereby providing a fracturing fluid containing a sufficient concentration of ozone to convert the subterranean organic compounds to the desired methanogenic digestible compounds.

If oxidation is not initiated during fracturing, then the oxidizing agent and water or a water-based fluid will be injected downhole. Ozone is a particularly suitable oxidizing agent as ozone can be easily added to water and water-based compounds by bubbling through the liquid prior to injection. In a preferred embodiment, at least two injection wells are used. One injection well delivers water to the subterranean coal seam and the other delivers the oxidizing agent to the coal seam. After injection downhole, the oxidizing agent reacts with the organic compounds of the coal typically yielding aldehydes, ketones and carboxylic acids. Thus, as oxidation proceeds, the pH of the fluid will drop. Although described in terms of at least two injection wells, those familiar with well operations will be able to readily use a single injection well in the performance of the present invention.

To permit pH monitoring of fluids during the oxidizing step, fluids may be extracted from the subterranean coal seam through one of the extraction wells. Alternatively, a pH monitor may be placed downhole in an extraction or injection well. Oxidation continues until the pH is less than 6. Typically, oxidation continues until the fluids extracted from the seam have reached a pH of 4 or less and the pH has stabilized. Stopping the oxidation step upon pH stabilization will minimize the loss of organic matter to undesirable carbon dioxide.

Following stabilization of effluent pH at a value of 4 or less, the fluid within the coal bed, referred to as effluent, contains compounds suitable for digestion by a methanogenic microbial community. As used herein the term "methanogenic microbial community refers to an inoculum containing bacteria and methanogenic archaea. In one embodiment of the present invention, effluent containing oxidation products may be pumped from the subterranean coal seam and stored or immediately transferred to a suitable incubator for digestion by a methanogenic microbial community.

To provide an environment conducive for methanogenesis, the present invention adjusts the pH of the effluent, before or after addition to the incubator, to a range of about 6 to about 8. More preferably, the pH within the incubator will be neutral. Alternatively, an optional buffer system may be added to the incubator or to the inoculum containing the methanogenic microbial community to protect the methanogenic microbial community from adverse pH conditions thereby eliminating the need to adjust the pH of the effluent. Thus, the buffer system maintains the pH of the solution containing the methanogenic microbial community within a range determined to maintain the bioactivity of the particular methanogenic microbial community. Following inoculation of the incubator with methanogenic microbial community, the conversion of the oxidation products to methane proceeds as discussed in more detail below to yield methane.

In Situ Oxidation and Methanogenic Conversion

In another embodiment, the present invention provides for carrying out the oxidation and methanogenic conversion of coal to methane in situ. Preferably, when practicing this embodiment the subterranean formation will have characteristics suitable for retaining and collecting gaseous compounds. This embodiment includes each of the steps discussed above. However, rather than extracting an effluent containing oxidation products followed by pH neutralization and incubation with a methanogenic microbial community, this embodiment provides for addition of the inoculum containing the methanogenic microbial community through the injection well(s) into the coal seam.

As in the above-discussed embodiment, injection of the inoculum into the subterranean coal bed will preferably occur after determining that the effluent has reached a pH of 4 or less. Upon determination of a stable pH in the desired range and following subsequent neutralization of the in situ effluent, a concentrated inoculum of methanogenic microbial community will be injected into the subterranean coal bed. Typically, the injection of methanogenic microbial community will be as an inoculum of microorganisms previously obtained from the site of interest or a specialty inoculum originally obtained from other locales and enriched for their ability to convert coal- or hydrocarbon-derived organic matter or the oxidation products of these materials to methane. The inoculation may or may not involve the use of carriers used to immobilize the inoculum of interest.

Following inoculation of the ozonated and pH adjusted coal seam with a methanogenic microbial community, the resulting methane can be collected and ultimately recovered. The inoculum of choice may also serve to directly convert coal organic matter to mineralized end-products including methane. Typically, completed incubation will start producing methane within a few days after inoculation.

Repetitive Cycles

Figure 7:
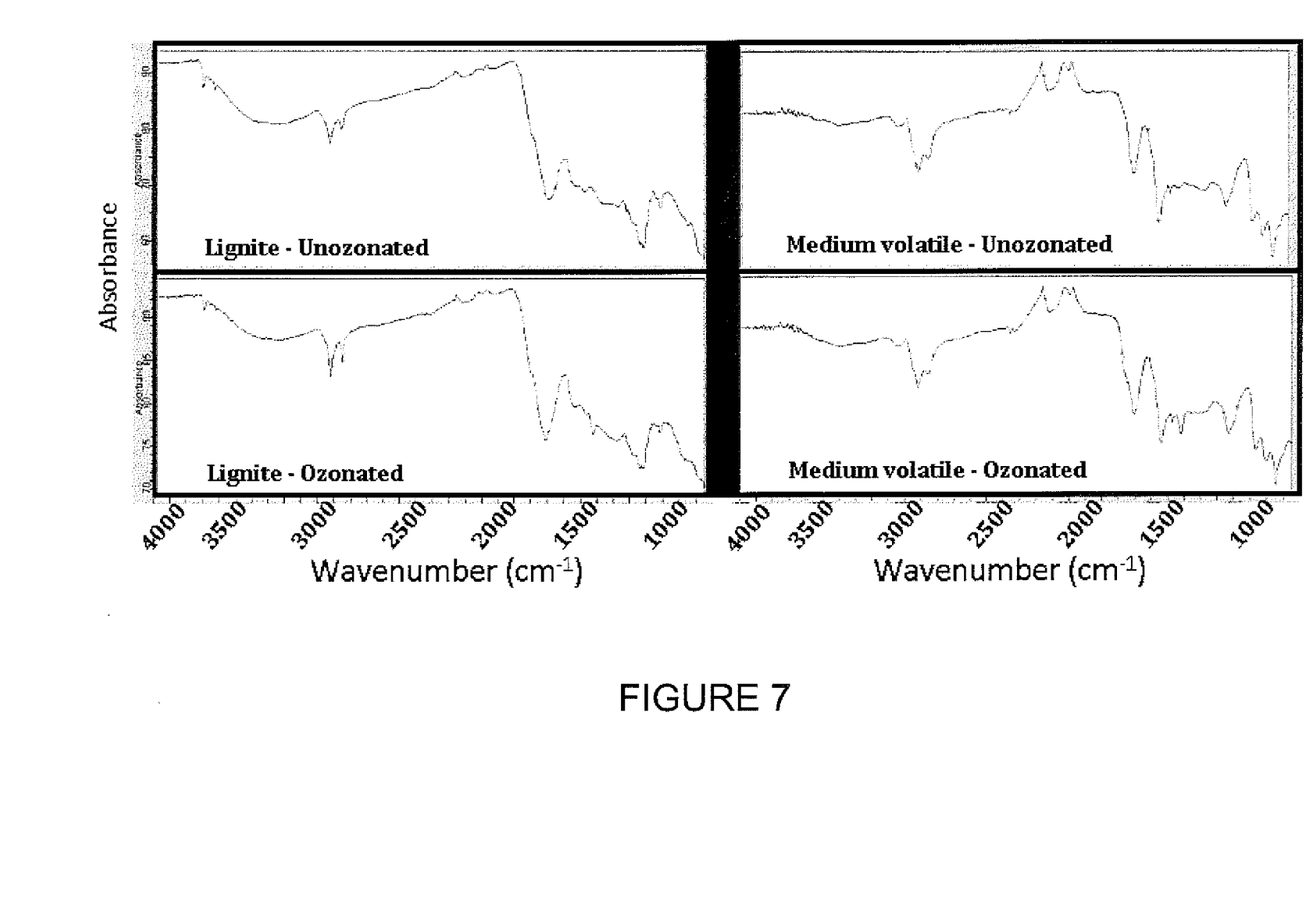
FIG. 7 depicts the infrared spectrum of lignite coal and medium volatile coal before and after ozonolysis.
Figure 8:
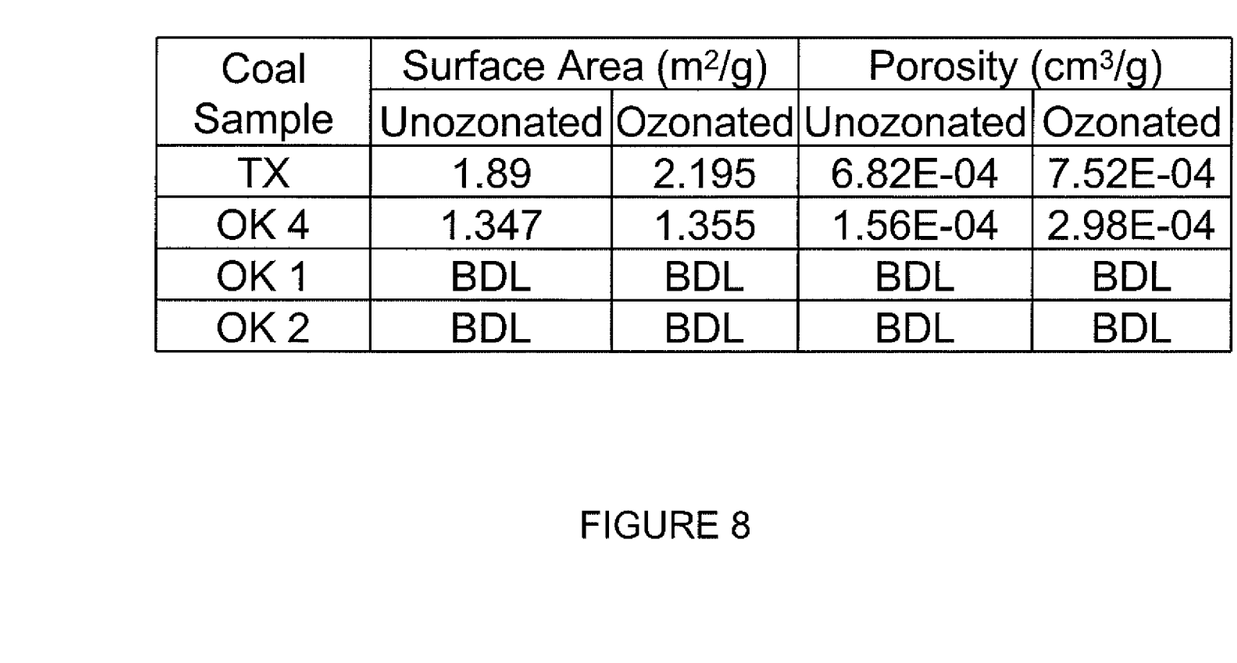
FIG. 8 depicts the surface area change following ozonolysis of a coal sample.

In each of the above embodiments, following the initial oxidation/methanogenic conversion cycle, the present invention also provides for repeated oxidation/methanogenic conversion cycles. When carrying out ozonolysis as the oxidation step, the ozone oxidizes the surfaces of the coal yielding water-soluble components. The oxidized compounds are subsequently found in the aqueous effluent. However, as represented by the data of FIGS. 7-8, ozonolysis does not substantially alter the surface chemistry of the remaining coal. Thus, the carbonaceous compounds in the remaining coal remain available for subsequent oxidation steps to further yield compounds suitable for methanogenic digestion. Advantageously, the water or water-based fluids used for the oxidation step may be repeatedly recycled during each additional oxidation step. Further, if desired, during the subsequent cycles of the present invention, additional fracturing of the coal seam may be carried out to provide the desired surface area and fluid permeability.

Thus, following the initial extraction of effluent from a coal seam treated according to the first method, the present invention provides for repeated oxidation treatments of the remaining in situ carbonaceous material. As noted above, oxidation will be carried out by injecting a fluid, typically water, into the coal seam. The injected fluid carries the oxidizing agent into contact with the coal. In one embodiment, the oxidation process utilizes two injection wells. One injection well provides the carrier fluid while the other injection well provides the oxidizing agent. In a preferred embodiment, one injection well provides water to the situ carbonaceous material and the other provides ozone. Preferably, the water then carries the injected ozone to the carbonaceous material.

Following oxidation of the subterranean organic compounds, as determined by pH monitoring, the effluent will contain compounds capable of supporting methanogenic digestion. The effluent is then extracted for subsequent methanogenesis treatment as described above. In each repeated cycle, oxidation preferably continues until the effluent has reached a pH of 4 or less. Additionally, this embodiment of the present invention provides for recycling of water for each subsequent oxidation treatment.

When practicing repetitive methanogenic digestion in the in situ environment, the initially produced methane will be removed via the extraction well. Thereafter, the steps of oxidation, pH monitoring, pH adjustment and inoculation with a methanogenic microbial community will be repeated.

Thus, following extraction of either the acidic effluent or the methanogenically produced methane, the present invention provides the option of repeating the oxidation and microbial conversion steps.

Oxidation and Methanogenic Conversion of Extracted Coal

The following discussion focuses on methanogenic conversion of previously extracted coal to methane. However, the biological and chemical processes occurring during the methanogenic conversion steps apply equally to methods discussed above.

To convert the organic compounds of coal, the present invention utilizes anaerobic microbial biodegradation processes. These processes rely upon microbial inocula having methanogenic capabilities. Bacteria suitable for use in this process include but are not limited to Lachnospiraceae, Clostridiaceae, Petoccacceae, Desulfobacterales; Syntrophobacterales and Desulfovibrionales. Such bacteria and the processes by which they anaerobically degrade organic matter are well known to those skilled in the art. Methanogenic bacteria suitable for use in the current method are also disclosed in the articles entitled "Bioenergy Production via Microbial Conversion of Residual Oil to Natural Gas," *Applied and Environmental Microbiology*, May 2008, Vol. 74, p. 3022-3029, Gieg, L., Duncan, K., and Suflita, J. incorporated herein by reference.

Figure 1:
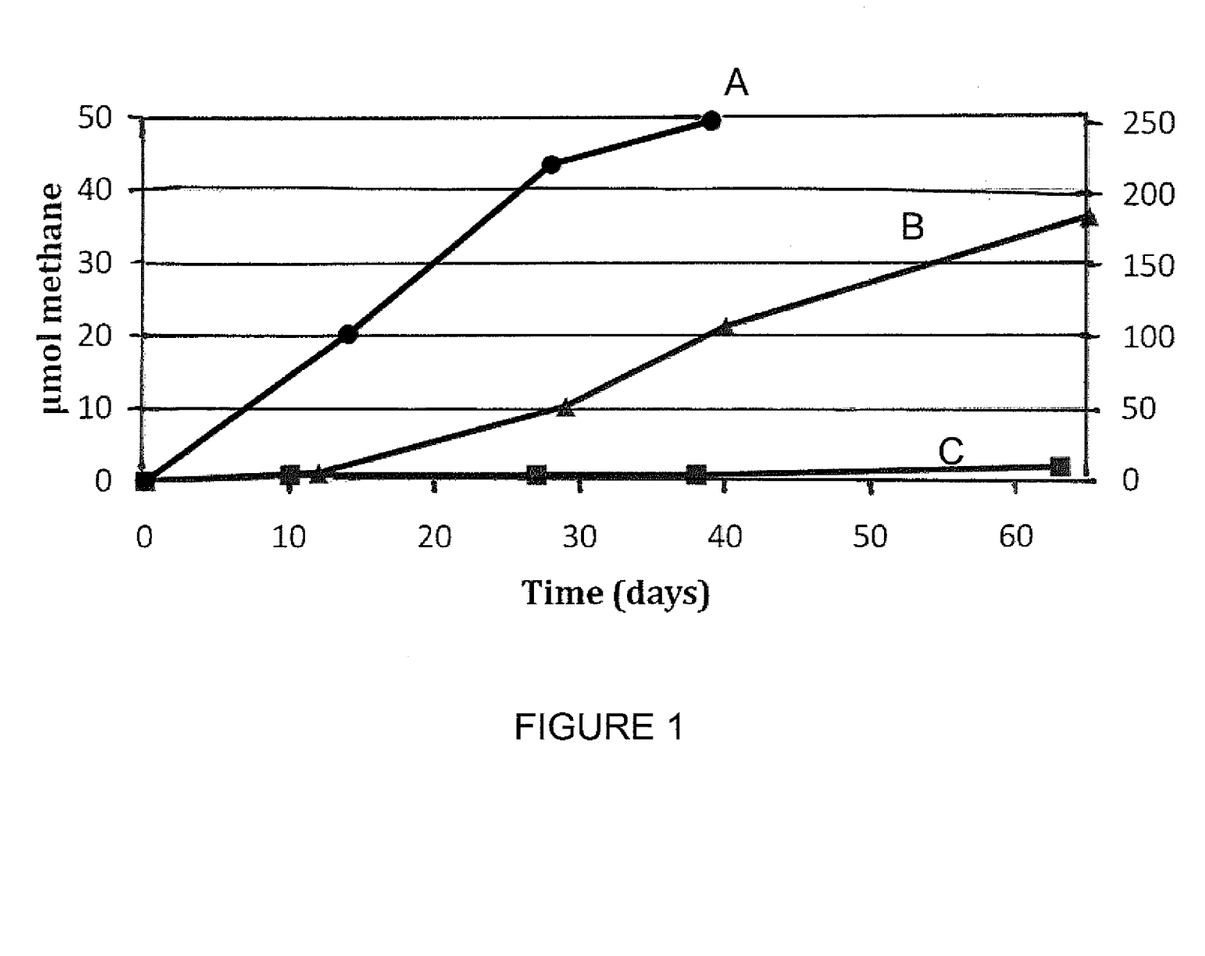
FIG. 1 depicts the results of Texas Lignite coal as treated in Example 1.
Figure 5:
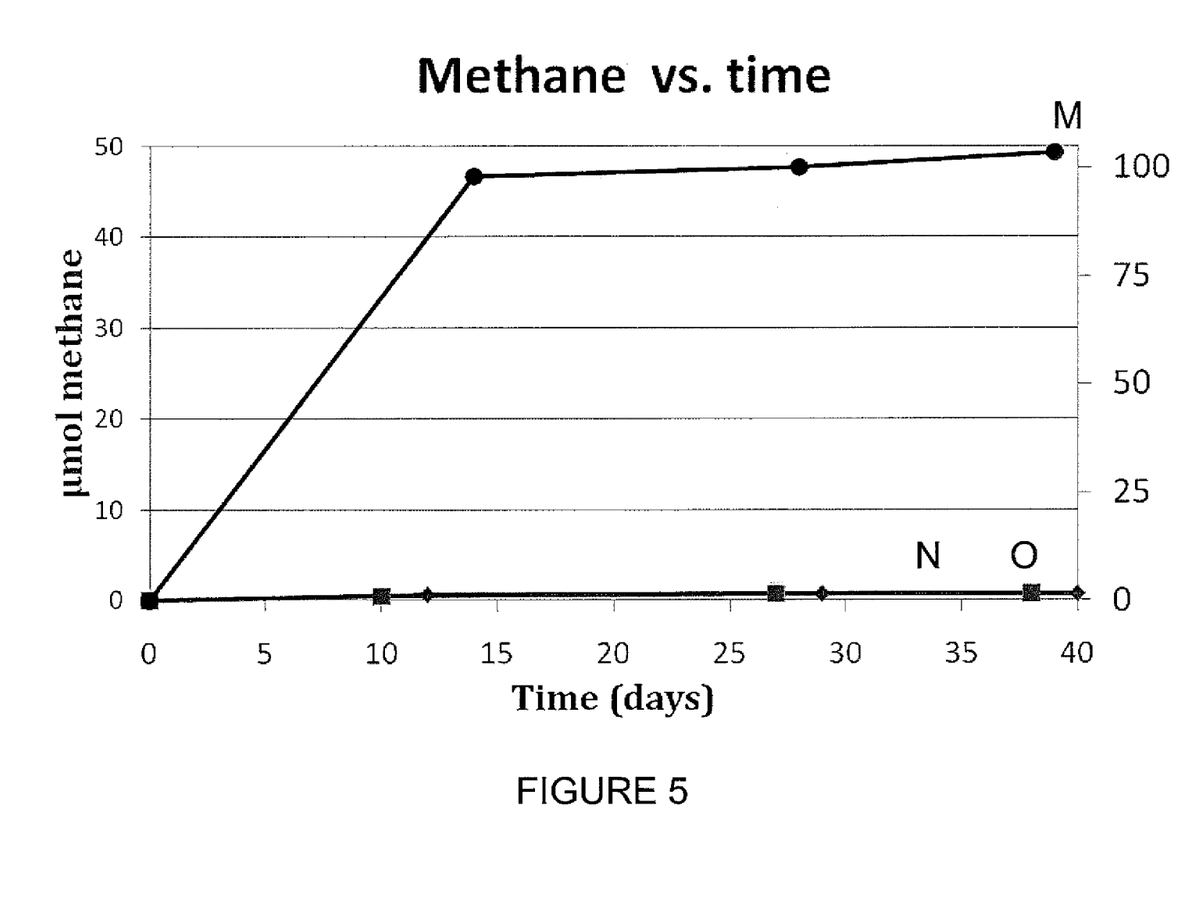
FIGS. 5 and 6 compare the production of methane from the effluent and from solid coal.
Figure 6:
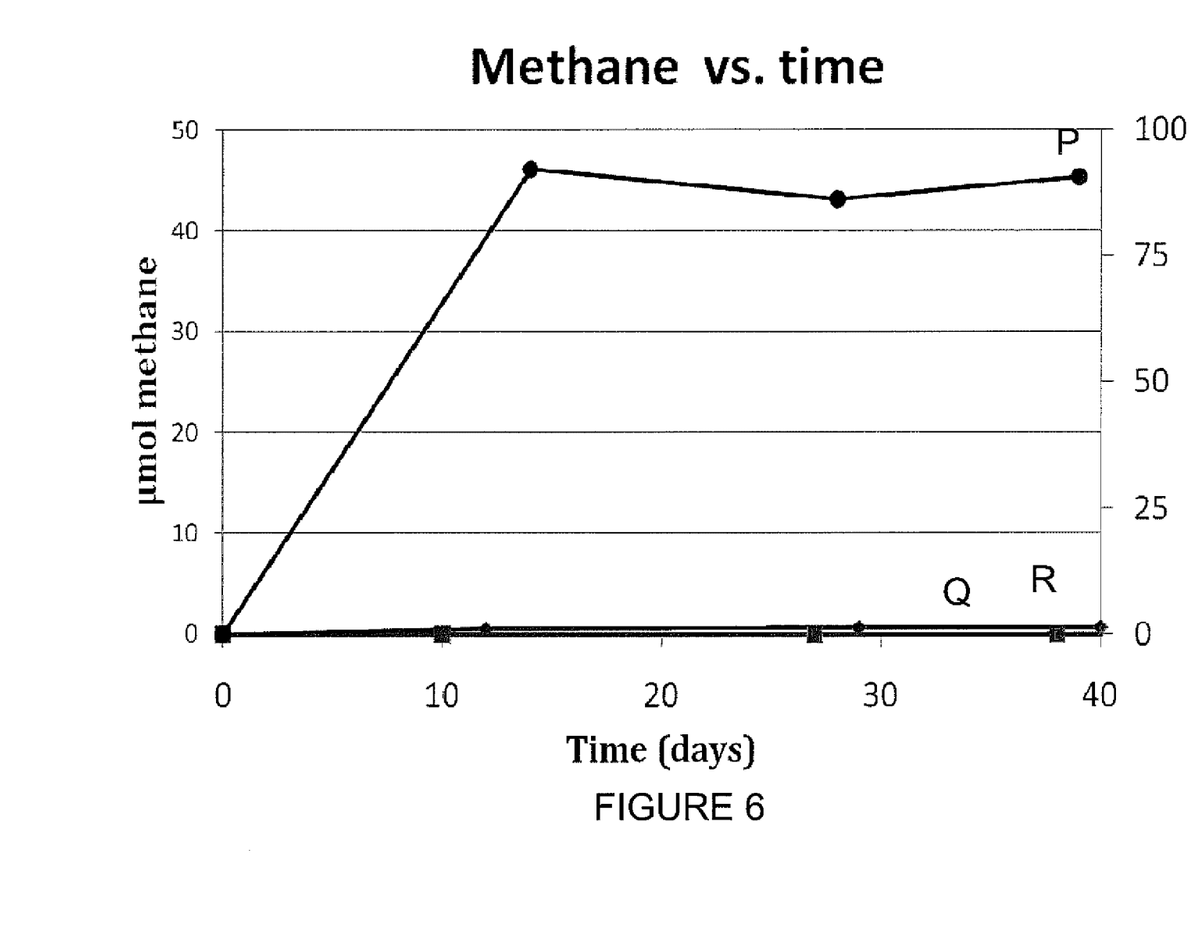

Additionally, unclassified bacteria can be prepared by methods known in the art for use in the method of the current invention. In general, one skilled in the art will be able to collect, cultivate and confirm the bioactivity of unclassified bacteria for methanogenic conversion of coal from formation waters, run-off and other local waters in the vicinity of coal beds. The collected unclassified bacteria forms the composition referred to herein as a "methanogenic microbial community." For example, the San Juan Basin has large deposits of coal and natural gas. Production waters from multiple wells within the San Juan Basin were combined to create a composite inoculum for use in Example 1 below. Waters of similar salinity were combined and centrifuged. Following centrifugation, the pelleted cells were recovered and resuspended in supernatant in a ratio suitable to provide a concentration of cells approximately ten times greater than present in the original waters. The observed conversion of organic material to methane in FIG. 1 demonstrates that production waters from regions containing large deposits of coal contain organisms suited for the method of the current. In FIG. 1, line A represents the conversion rate of oxidized compounds in effluent to methane (7.9 μmol methane/day), line B represents conversion of ozonated coal (0.35 μmol methane/day), and line C represents conversion of unozonated coal (0.02 μmol methane/day). As demonstrated by the results of FIGS. 5 and 6 a methanogenic microbial community originally selected for the ability to digest residue oil in subsurface formations will also perform satisfactorily in the methods of the present invention. In FIG. 5, line M represents methane production from the effluent (3.57 μmol/day) and lines N and O represent methane production from ozonated and unozonated coal (both 0.02 μmol/day). Similarly, in FIG. 6, line P represents methane production from the effluent (3.1 μmol/day) and lines Q and R represent methane production from ozonated and unozonated coal (both 0.02 μmol/day).

When practicing the method of the current invention on previously extracted coal, winding of the coal to increase surface area will enhance the oxidation step. Although particle size is not critical to the oxidation step (or ozonolysis), the number of repetitive cycles may be reduced by increasing the surface area available for oxidation. In general, the preferred particle size is from about 150 μm to about 1.17 mm. Most preferably, the coal particles will have sizes ranging from about 210 μm to about 500 μm.

When working with extracted coal particles and using ozonolysis to carry out the oxidation step, collection of the desired products can be enhanced by preparing a slurry of coal in water. In one embodiment, following preparation of the slurry, ozonolysis occurs by bubbling ozone through the slurry at a rate sufficient to oxidize at least a portion of the hydrocarbons within the coal. Typical flow rates may be up to about 2 L of ozone/min for bench scale operations and scaled accordingly for field and industrial operations. In general, ozonolysis occurs at a flow rate of about 1.6 L of ozone/min. During the ozonolysis process, the pressure is generally kept less than 20 psi. Typically, the ozonolysis process occurs at a pressure of about 17 psi. Stirring of the slurry will enhance the efficiency of the reaction. The exposure time of the ozonolysis step is between 30 min and 4 hours, with preference to the shorter exposure time to minimize the abiotic mineralizaton of the coal organic matter. Although the process steps are not significantly impacted by temperature, when practicing the current invention in the laboratory or on using an industrial scale fermenter, the temperature will generally be maintained between about 20° C. and about 50° C. More preferably, to enhance methanogenesis, the fermenter or incubator temperatures will be between about 20° C. and 40° C. Other temperature ranges may be preferred; however, one skilled in the art will be able to readily determine the optimum operational temperature for the inoculum. Further, flow rates and pressures may vary with different operational scales.

Although the foregoing process has been described with the use of water or water-based slurries and oxidation carrier fluids, the present invention may also be carried out with brine solutions with saline concentrations up to 20% depending upon the methanogenic microbial community selected for methane generation.

In order to produce an effluent best suited for the methanogenic process, the method of the current invention monitors the slurry's pH during the oxidation step. Preferably, the oxidation process stops when the slurry pH achieves a steady acidic pH, generally a pH of less than 6. More typically oxidation stops at a pH value of 4 or less. Regular monitoring of the slurry pH will minimize loss of organic material to carbon dioxide due to excessive oxidation.

Upon reaching the target pH, oxidant flow to the slurry is halted. The slurry is filtered to isolate the effluent from the solid particulate matter. To provide conditions conducive for methanogenesis within the fermenter, the present invention adjusts the pH of the effluent before or after addition to the fermenter to a range of about 6 to about 8. More preferably, the pH within the fermenter will be neutral. Alternatively, an optional buffer system may be added to the fermenter or to the inoculum containing the methanogenic microbial community to protect the methanogenic microbial community from adverse pH conditions thereby eliminating the need to adjust the pH of the effluent prior to addition of the inoculum. Thus, the buffer system maintains the pH of the solution containing the methanogenic microbial community within a range determined to maintain the bioactivity of the particular methanogenic microbial community.

Figure 3:
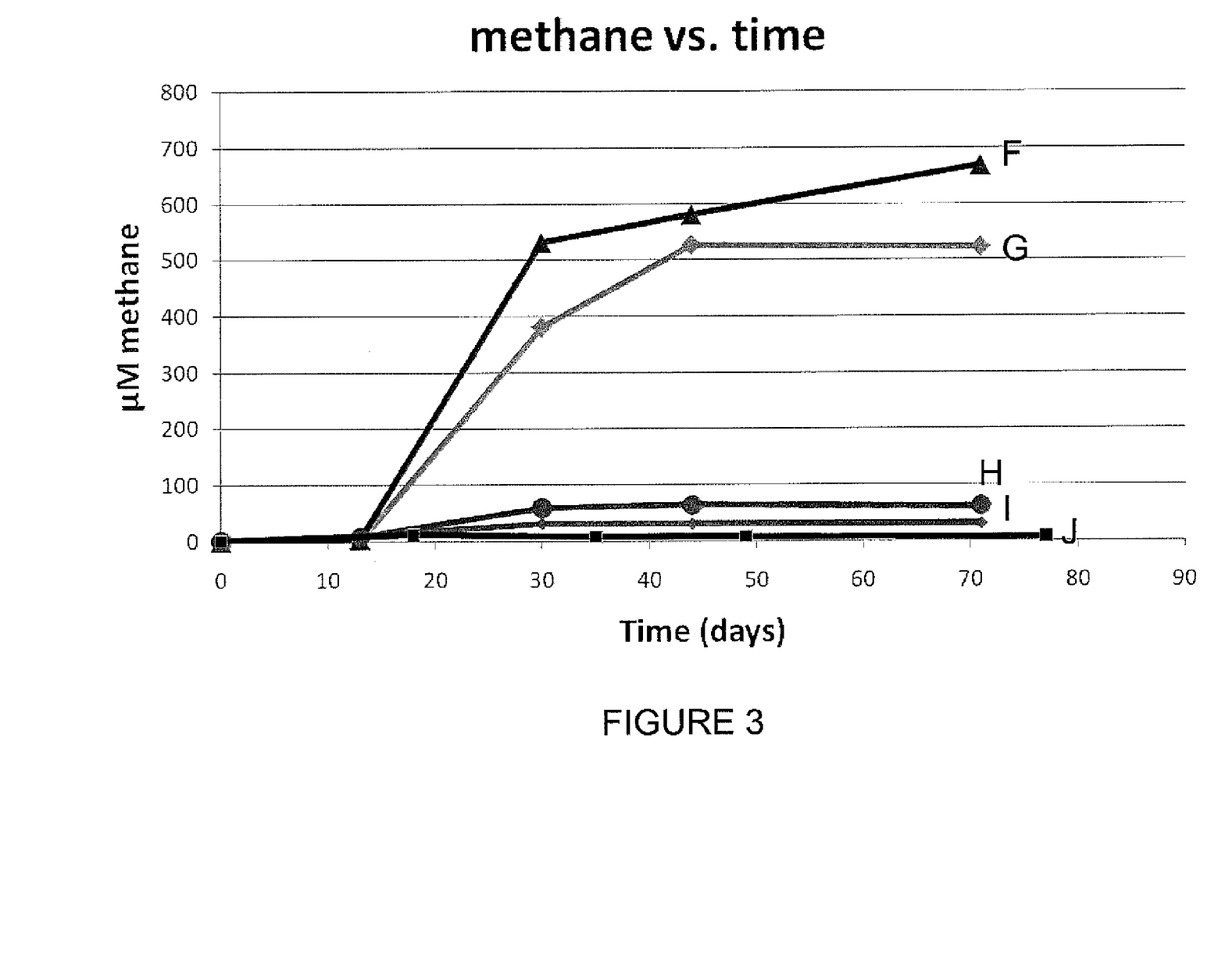
FIG. 3 depicts the production rate of methane from the effluent of ozonated coals using oil-degrading methanogenic microbial community.
Figure 4:
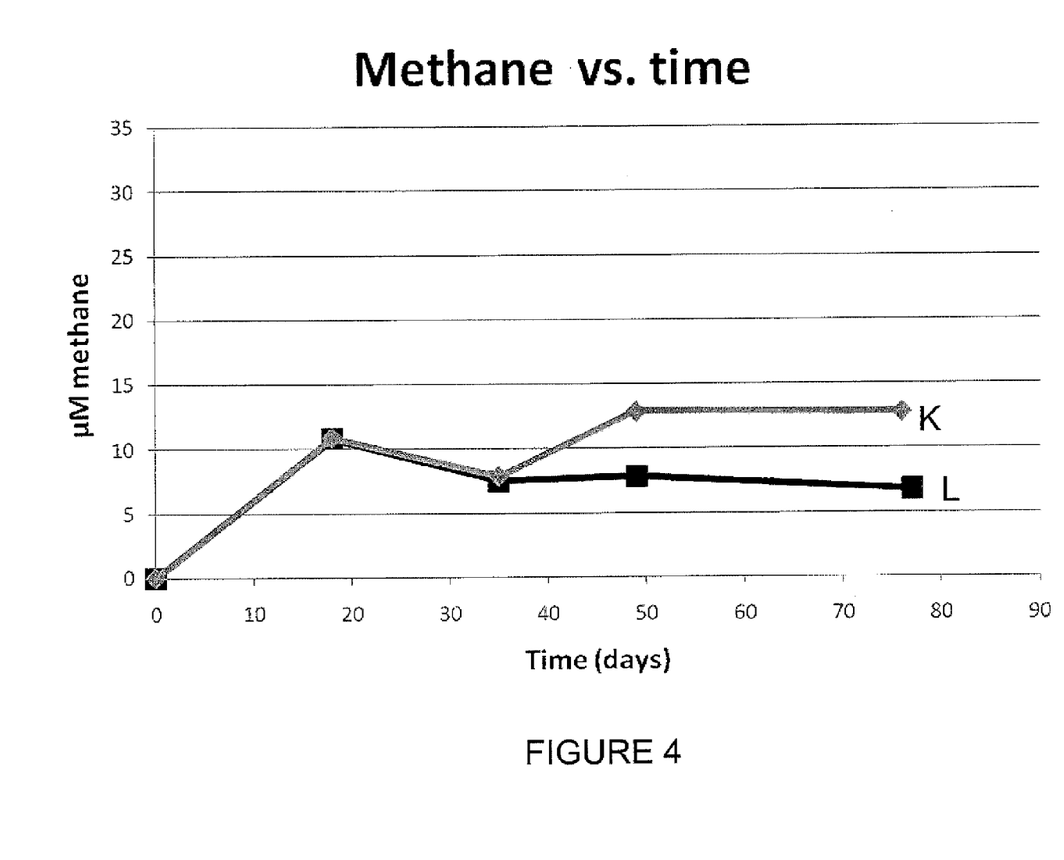
FIG. 4 depicts the production rate of methane from the solid particulate material of mildly ozonated coals using oil-degrading methanogenic microbial community.
Figure 9:
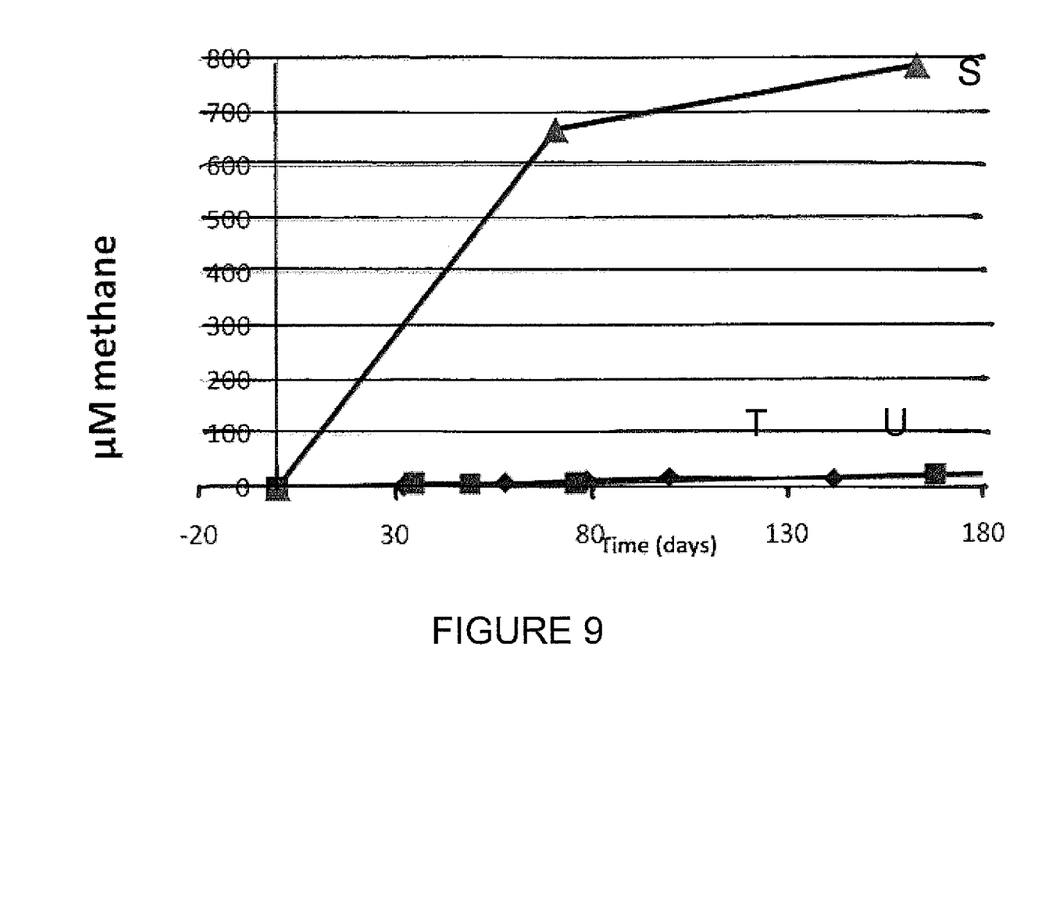
FIG. 9 depicts the methane production rate from coal following oxidation and exposure to a methanogenic microbial community prepared from a composite inoculum obtained by concentrating cells from major U.S. coal basins.
Figure 10:
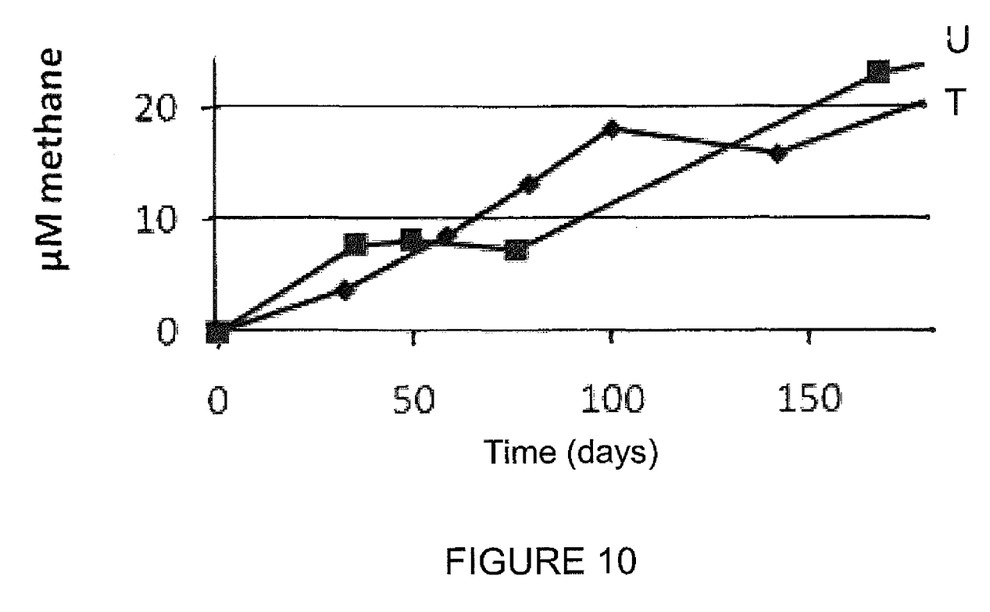
FIG. 10 depicts lines T and U from FIG. 9 on a larger scale.

As depicted in FIGS. 1, 3, 5-6 and 9, the effluent contains the majority of oxidized compounds suitable for methanogenic conversion to methane. FIG. 10 reflects some methanogenic process as occurring in the mildly oxidized solid coal particles (FIG. 10, line T) and in non-oxidized solid coal particles (FIG. 10, line U). FIG. 4 also depicts some methane production from ozonated particulate coal (FIG. 4, lines K and L). As discussed above, FIGS. 1, 5 and 6 depict methane production from effluent at rates of 7.9 µmole/day, 3.57 µmol/day and 3.1 µmol/day respectively. In FIG. 3, lines F-I represent methane production from differing samples of coal (line F=OPL 1184, line G=OPL 1183, line H=a New Mexico coal sample, line I=OPL 1090, a lignite). Line J is a blank containing no coal. Finally, FIGS. 8 and 9 depict conversion to methane using a methanogenic microbial community prepared from a composite inoculum obtained by concentrating cells from major U.S. coal basins. As reflected therein, line S indicates a conversion to methane at a rate of 32.5 µM/g/day and lines T and U generally indicate conversion at a rate of 0.05 µM/g/day. OPL 1183 refers to a high volatile bituminous coal sample obtained from Nowata County, Oklahoma. OPL 1090 refers to a lignite coal sample obtain from Robertson County, Texas. OPL 1184 refers to a high volatile bituminous coal sample obtained from Craig County, Oklahoma. OPL 1342 refers to a medium volatile bituminous coal sample obtained from Le Flore County Oklahoma. OPL 1344 refers to a low volatile bituminous coal sample obtained from Le Flore County Oklahoma.

The actual formulae of the resulting oxidation products are not critical, provided that the products support methanogenesis, thereby enabling conversion by a methanogenic microbial community of the resulting products to methane Following the mild oxidation step, the effluent is combined with the inoculum containing bacteria and methanogenic archaea. As used herein, the term mild oxidation refers to a process that minimizes the time and amount of oxidant that will yield a stable, acidic effluent. The resulting pH should be less than 6, more typically the resulting pH is about 4 or less. As previously noted, mild oxidation generally stops the conversion of the organic material upon achieving a stable pH of less than 4 thereby substantially precluding the generation of carbon dioxide. Thus, the method of the present invention preserves the unreacted organic compounds of coal for subsequent oxidation while providing oxidation compounds suitable for methanogenic conversion to methane. Following neutralization to a pH between about 6-8, subsequent methanogenic degradation of the oxidation products produces a detectable concentration of methane. The resulting methane can be continuously collected or allowed to accumulate over a period of time prior to collection. Typically, the oxidation process will be an ozonolysis process.

Finally, as discussed above in each in situ embodiments, the oxidation/methanogenic conversions steps for converting extracted coal to methane may be repeated multiple times to enhance the conversion of coal to methane. In this embodiment, the repeated steps provide for re-slurrying the solid coal particles with water, water-based fluid, brine, or brine-based fluids followed by oxidation, isolation of oxidized compounds and methanogenic conversion.

EXAMPLES

The following example demonstrates the methods of the current invention. The results of Example 1 are provided in FIG. 1. This example utilized inoculum prepared from production waters of the San Juan Basin. As discussed above cell pellets were isolated by centrifugation and subsequently resuspended to produce a concentration of bacterial cells ten times greater than normally found in the production waters. Coal samples from the San Juan Basin as well as other regions such as coal fields in Oklahoma, Texas and New Mexico were used in this test. These coals had different hardness values, sulfur and volatile organic matter contents. The coals were ground, slurried and subjected to ozonolysis. The ozonolysis continued until the effluent reached a stable pH of ≤4.

To determine the degree of anaerobic degradation provided by the prepared inoculum, samples bottles were prepared with each containing either two grams of coal or an amount of effluent generated from 2 grams of coal using the outlined procedure and two milliliters of a concentrated inoculum. Twenty milliliters of a microbiological medium was added to provide for cultivation of the anaerobes. Negative controls were also prepared that included sterile preparations, where the inoculum was destroyed by autoclaving, coal-free incubations (no coal incubations) and no inoculum controls. All preparations were interpreted relative to unozonated coal.

The unozonated coal sample produced 0.02 µmol methane/day. In contrast, the effluent portions of the coals subjected to the ozonolysis step produced methane at a rate of ~3 µmol methane/day. For the Texas lignite sample depicted in FIG. 1, the solid coal particles produced methane at a rate somewhat faster than the unozonated coal, i.e. a rate of 0.35 µmol/day.

In Example 2 the organisms used as inoculum and the cultivation methods are described in "Bioenergy Production via Microbial Conversion of Residual Oil to Natural Gas," *Applied and Environmental Microbiology*, May 2008, Vol. 74, p. 3022-3029, Gieg, L., Duncan, K., and Suflita, J. incorporated herein by reference.

In FIG. 3, the coal material ranged between lignitic and high volatile bituminous, as discussed above. The coals were ground and sieved to obtain a particle size of 210-500 microns. Five grams of coal were weighed and diluted with 150 ml of nanopure water to form a slurry. Ozone was bubbled into solution at a rate of 1.6 L/min and a pressure of 17 psi. Measurements of pH were performed every 15 minutes while the solution was magnetically stirred and ozone was continuously administered. Following establishment of the desired pH (a stable pH typically about ≤4), the solution was vacuum filtered using a 0.45 µm membrane filter and separated into ozonated particulate coal and an aqueous effluent. The effluent was filter sterilized and stored in sterile anoxic serum bottles, at 4° C. in the dark. Sterile 160 ml serum bottles received 5 ml inoculum and 20 ml of reduced, bicarbonate-buffered fresh water mineral medium, pH 7.2-7.4. Mildly oxidized coal effluents were added after inoculation in a concentration equivalent to 0.1 g coal/ml. The bottles were sealed with butyl rubber stoppers, secured with aluminum crimp seals and incubated under a $N_2$:$CO_2$ (80:20) headspace at room temperature (22°±2 C). The results with this defined inoculum were roughly equivalent to that observed with the undefined inoculum.

Figure 2:
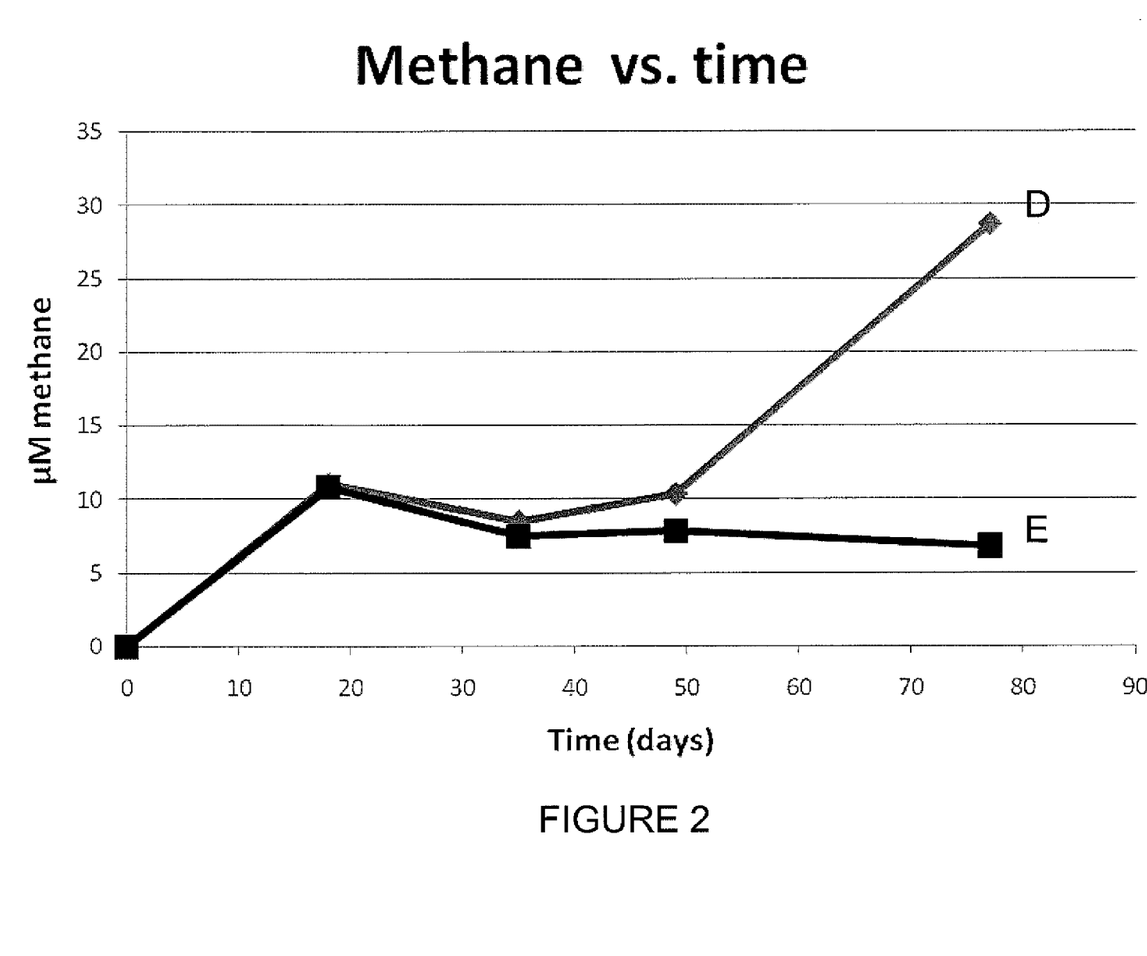
FIG. 2 depicts the production rate of methane over time from unozonated coal using oil-degrading methanogenic microbial community.

The foregoing examples demonstrate the ability of the present invention to use inocula containing methanogenic archaea and anaerobic bacteria to produce methane from coal subjected to ozonolysis. The aqueous effluent produced by the ozonolysis step produced the highest methane production as compared to the solid coal particles. As to methanogenic conversion of unozonated solid coal particles, higher rates were typically seen with regard to softer coals. See FIG. 2. However, more dramatic increases in methane production rates and yields were observed when harder coals were subjected to the process compared to softer coals that were already partially oxidized.

Other embodiments of the current invention will be apparent to those skilled in the art from a consideration of this specification or practice of the invention disclosed herein. Thus, the foregoing specification is considered merely exemplary of the current invention with the true scope and spirit of the invention being defined by the following claims.

We claim:

1. A method for converting coal to methane comprising the steps of:
    forming a slurry of coal particles and a liquid;
    combining an oxidizing agent with the slurry causing oxidation of at least a portion of the coal particles of the slurry and producing oxidation products;
    monitoring the pH of the slurry;
    collecting an effluent of the slurry when the slurry reaches a pH in a range from about 4 to less than 6, said effluent of the slurry containing the oxidation products to be converted to methane; and
    converting at least a portion of said oxidation products to methane by combining the effluent having the oxidation products with an inoculum containing a methanogenic microbial community and allowing said methanogenic microbial community to digest said oxidation products.

2. The method of claim 1, wherein the addition of oxidizing agent to the slurry is stopped when the slurry reaches the pH in a range from about 4 to less than 6.

3. The method of claim 1, further comprising the steps of:
    after collecting the effluent of the slurry, adding additional liquid to reconstitute the slurry of coal particles;
    repeating the steps of combining an oxidizing agent with the slurry, monitoring the pH, and collecting the effluent of the slurry.

4. The method of claim 1, following the step of collecting the effluent of the slurry, further comprising the step of adjusting the pH of the effluent to be in a range between about 6 and about 8.

5. The method of claim 1, wherein the inoculum containing methanogenic microbial community further contains a buffer system selected to maintain the inoculum containing methanogenic microbial community within a pH range determined to maintain bioactivity of the methanogenic microbial community.

6. The method of claim 1, wherein the coal particles have a particle size in a range from about 150 µm to about 1.17 mm.

7. The method of claim 1, wherein in the step of combining an oxidizing agent with the slurry, the slurry is maintained at a temperature in a range between about 20° C. and 50° C.

8. The method of claim 1, wherein the effluent of the slurry is collected when the slurry reaches a pH of about 4.

9. The method of claim 1, wherein the oxidizing agent is ozone.

10. The method of claim 1, wherein the oxidizing agent is hydrogen peroxide.

11. The method of claim 1, wherein in the step of combining an oxidizing agent with the slurry, the oxidizing agent is ozone and is passed through the slurry at a flow rate of about two liters per minute.

12. The method of claim 1, wherein the liquid used to produce a slurry is selected from the group consisting of water and brine.

13. A method for converting coal to methane comprising the steps of:
    forming a slurry of coal particles and a liquid;
    combining ozone with the slurry thereby causing oxidation of at least a portion of the coal particles and producing oxidation products, wherein the slurry is maintained at a temperature in a range between about 20° C. and 50° C.;
    monitoring the pH of the slurry;
    collecting an effluent of the slurry when the slurry reaches a pH in a range from about 4 to less than 6, said effluent of the slurry containing the oxidation products to be converted to methane; and
    converting at least a portion of said oxidation products to methane by combining the effluent having the oxidation products with an inoculum containing a methanogenic microbial community and allowing said methanogenic microbial community to digest said oxidation products.

14. The method of claim 13, wherein the combining of the ozone to the slurry is stopped when the slurry reaches the pH in a range from about 4 to less than 6.

15. The method of claim 13, further comprising the steps of:
    after collecting the effluent of the slurry, adding additional liquid to reconstitute the slurry of coal particles;
    repeating the steps of combining ozone with the slurry, monitoring the pH, and collecting the effluent of the slurry.

16. The method of claim 13, following the step of collecting the effluent of the slurry, further comprising the step of adjusting the pH of the effluent to be in a range between about 6 and about 8.

17. The method of claim 13, wherein the inoculum containing methanogenic microbial community further contains a buffer system selected to maintain the inoculum containing methanogenic microbial community within a pH range determined to maintain bioactivity of the methanogenic microbial community.

18. The method of claim 13, wherein the coal particles have a particle size in a range from about 150 µm to about 1.17 mm.

19. The method of claim 13, wherein the effluent of the slurry is collected when the slurry reaches a pH of about 4.

20. The method of claim 13, wherein in the step of combining ozone with the slurry, the ozone is added to the slurry at a flow rate of about two liters per minute.

21. The method of claim 13, wherein the liquid used to produce a slurry is selected from the group consisting of water and brine.

* * * * *